(12) United States Patent
Kuijper

(10) Patent No.: US 10,744,221 B2
(45) Date of Patent: Aug. 18, 2020

(54) AIR SCENTING ASSEMBLY

(71) Applicant: Common Sense Holding B.V., Tilburg (NL)

(72) Inventor: Ewoud Kees Kuijper, Tilburg (NL)

(73) Assignee: COMMON SENSE HOLDING B.V., Tilburg (Nl)

( * ) Notice: Subject to any disclaimer, the term of this patent is extended or adjusted under 35 U.S.C. 154(b) by 0 days.

(21) Appl. No.: 16/518,467

(22) Filed: Jul. 22, 2019

(65) Prior Publication Data

US 2019/0343976 A1 Nov. 14, 2019

Related U.S. Application Data

(63) Continuation of application No. 15/534,061, filed as application No. PCT/NL2015/050851 on Dec. 9, 2015, now Pat. No. 10,363,334.

(30) Foreign Application Priority Data

Dec. 9, 2014 (NL) ..................................... 2013945

(51) Int. Cl.
*A61L 9/03* (2006.01)
*A61L 9/14* (2006.01)
(Continued)

(52) U.S. Cl.
CPC ............... *A61L 9/032* (2013.01); *A61L 9/035* (2013.01); *A61L 9/042* (2013.01); *A61L 9/122* (2013.01);
(Continued)

(58) Field of Classification Search
CPC .......... A61L 9/032; A61L 9/035; A61L 9/122; A61L 9/042; B01F 3/04; B01F 3/04085
(Continued)

(56) References Cited

U.S. PATENT DOCUMENTS

| 4,407,585 A | 10/1983 | Hartford et al. |
| 6,390,453 B1 * | 5/2002 | Frederickson ........ A61M 15/02 261/100 |
| 2007/0095941 A1 * | 5/2007 | Gorres ................ A01M 31/008 239/337 |

FOREIGN PATENT DOCUMENTS

| EP | 1649747 A1 | 4/2006 |
| JP | 05146499 A | 6/1993 |

OTHER PUBLICATIONS

International Search Report for corresponding International Application No. PCT/NL2015/050851 dated May 23, 2016.
(Continued)

*Primary Examiner* — Robert A Hopkins
(74) *Attorney, Agent, or Firm* — Renner, Otto, Boisselle & Sklar, LLP

(57) ABSTRACT

An air scenting assembly includes: a scent container which at least initially contains a scent perfume, and a scent perfume extracting mechanism, which is configured to release scent perfume from the scent container. The scent perfume extracting mechanism includes a scent perfume absorbing element insertable into said scent container, a scent carrying material, a dripping mechanism arranged onto said scent perfume absorbing element, said dripping mechanism is configured to deposit scent perfume from the scent container onto said scent carrying material, and a limiter to restrain extraction of scent perfume from the scent container, wherein the limiter comprises an air duct between the scent perfume absorbing element and the dripping mechanism, and the limiter is air flow controlled, wherein one end of said air duct is placed inside said scent container, and wherein the other end of said air duct is connected to a nozzle, said nozzle being arranged on said scent carrying material so that when said scent carrying material is drenched to saturation, no more air can pass through said scent carrying material
(Continued)

and up into said nozzle and said air duct, and so that when the scent carrying material is dry enough passage of air through said air duct is allowed.

7 Claims, 15 Drawing Sheets

(51) Int. Cl.
*A61L 9/12* (2006.01)
*A61L 9/04* (2006.01)
*B01F 3/04* (2006.01)

(52) U.S. Cl.
CPC ............ *A61L 9/14* (2013.01); *B01F 3/04085* (2013.01); *A61L 9/125* (2013.01); *A61L 2209/11* (2013.01); *A61L 2209/111* (2013.01); *A61L 2209/133* (2013.01); *A61L 2209/134* (2013.01); *A61L 2209/135* (2013.01)

(58) Field of Classification Search
USPC .............. 261/30, DIG. 88, DIG. 89; 422/124
See application file for complete search history.

(56) References Cited

OTHER PUBLICATIONS

Written Opinion of the International Searching Authority for corresponding International Application No. PCT/NL2015/050851 dated May 23, 2016.
International Preliminary Report on Patentability for corresponding International Application No. PCT/NL2015/050851 dated Apr. 24, 2017.

* cited by examiner

AIR SCENTING ASSEMBLY

This application is a continuation of U.S. application Ser. No. 15/534,061 filed Jun. 8, 2017, which is a national phase of International Application No. PCT/NL2015/050851 filed Dec. 9, 2015 and published in the English language, which claims priority to NL Application No. 2013945 filed Dec. 9, 2014.

The present disclosure relates to an air scenting assembly, comprising a scent container which at least initially contains a scent perfume, and a scent perfume extracting mechanism.

Air scenting devices in a prior art form are known to comprise containers of scent perfumes, into which dissemination elements, such as absorber sticks, can be inserted. Thereby, scent perfume can be drawn up through the dissemination element to be freed into the air in a space, such as a room of a house or a space of a building in general. Such prior art air scenting devices have a number of drawbacks and/or shortcomings, in terms of structure, use possibilities and/or other aspects.

For example, dissemination elements are passive in that these can not be regulated with respect to amounts of scent perfumes that can be freed into the air. Any one dissemination element can even perform differently under changed circumstances. Further, users are restricted to offered scent perfumes in each single container. Combinations of scents are only the ones available in pre-mixed scent perfumes or are possible by positioning more prior art scenting devices, with a risk of over-scenting the air in a room.

Additionally reference is made here to U.S. Pat. No. 4,407,585, which discloses a clock, with an alarm to alert users by using scented air, which is generated when the alarm goes off. Instead of or in addition to generating an alarm, scented air is expelled from a clock's housing. Scented air is expelled from the known housing through an opening which is arranged in full view in a side wall of the housing, in order to minimize the time for expelled scented air to become noticeable to users from the moment the alarm goes off. However, the resulting appearance of the device known from this disclosure much resembles a cuckoo clock, where users would expect the cuckoo to come out of the hole defining the air outflow opening to indicate the time of day with a successive number of bird sounds. Further, the device known from U.S. Pat. No. 4,407,585 has a perfume dispensing mechanism to selectively release a scent perfume into a perfume absorber, like a bowl filled with a dot of cotton wool or the like, which is only responsive to the alarm control, and releases perfume at the time an alarm goes off. Such a control does not take into account whether such an absorber has dried up through evaporation of the perfume. If the alarm is set to go off at relatively short intervals, the known device cannot take into account if the absorber is already saturated and scent perfume is dispensed in or on the absorber, even if that would result in the oversaturation and/or overflow of the absorber and any bowl or the like with the absorber therein. Further, the device known from U.S. Pat. No. 4,407,585 doesn't provide any degree of versatility, for example in terms of different scents and combinations thereof, for scenting air. In summary, the device known from U.S. Pat. No. 4,407,585 is only suitable for use as or in combination with a clock, lacks in versatility, and can run dry or overrun with scent perfume, if managed like a clock, whilst practically continuous scenting air is desired.

According to the present disclosure, an air scenting assembly according to claim 1 is provided.

The provision of an optional mixing chamber allows for greater control over the release of scent perfume into the air, by generating in the mixing chamber a mixture of air and scented perfume, i.e. the scented air. For example valves and fans can be employed in association with such mixing chambers to allow such greater control. If a mixing chamber is combined for more than one scent module and the accommodations into which these scent modules are accommodated, access from the accommodations to the mixing chamber, for example using valves or the like, can contribute to a precise control over the nature and smell of the scented air to be expelled into the room or space. Many such embodiments are possible within the framework of the present disclosure, and some of these are discussed below, and/or defined in the appended claims, or may be considered to lie within the grasp of the skilled person after having been informed of the basic general idea of the present disclosure.

In a potential embodiment, the air scenting device according to the present disclosure may exhibit the additional feature of a fan in communication with the chamber and the outside of the housing, wherein the fan is configured to expel, when activated, scented air from the chamber.

In a potential embodiment, the air scenting device according to the present disclosure may exhibit the alternative or additional feature that the accommodation comprises a latch or locking mechanism to at least temporarily engage an inserted scent module. In such an embodiment, optionally, the latch or locking mechanism comprises a magnet.

In a potential embodiment, the air scenting device according to the present disclosure may exhibit the alternative or additional feature that the outflow opening is oriented downward, out of the housing relative to the chamber. This may serve to hide the outflow opening from view. In such an embodiment the air scenting device may further comprising a foot configured to support housing thereon, wherein the foot exhibits a smaller horizontal circumferential size than the housing and the outflow opening is arranged in or at least partially around the foot. The foot may configured to support housing thereon. The foot has a smaller horizontal circumferential size than the housing and the outflow opening is arranged at least partially around the foot. The outflow opening may be arranged additionally or alternatively in the foot, if interiors of the housing and foot are in open air flow connection. In case the outflow opening is in an underside of the housing, at least partially around the foot 4, or in a side wall of foot 4, the blowout opening may be at least partially and preferably fully hidden from sight.

In a potential embodiment, the air scenting device according to the present disclosure may exhibit the alternative or additional feature of a scent perfume extracting mechanism configured to transfer scent perfume from the scent module into the chamber. In such an embodiment, optionally, the scent perfume extracting mechanism comprises a dripping mechanism in combination with a scent perfume absorbing element, onto which the dripping mechanism is arranged to deposit scent perfume from the scent module. In such an embodiment, optionally, the dripping mechanism comprises a scent extracting absorber, configured to extend into a container of the scent module, wherein the container carries the scent perfume. In an embodiment having a scent perfume extracting mechanism, optionally, the scent perfume extracting mechanism comprises a limiter to restrain extraction of scent perfume from the scent module. In an embodiment having a dripping mechanism and the limiter, optionally, the limiter comprises an air duct between the perfume absorbing element and the dripping mechanism, and the limiter is air flow controlled.

In a potential embodiment, the air scenting device according to the present disclosure may exhibit the alternative or additional feature of at least one heater associated with the accommodation, and configured to facilitate extraction of scent perfume from the scent module.

In a potential embodiment, the air scenting device according to the present disclosure may exhibit the alternative or additional feature of at least one control. Such a control may control valves and/or fans, and do so for example based on a determined nature of a scent perfume in a connected scent module, and can even take compatibility of distinct scents into account, or mixing ratios to achieve the most pleasant resulting scented air in a room or space. Such a control may have communication means to accept input from a user, to start scenting air, change a mixture of scent perfumes, and the like. Such a communication could even be an app on a mobile device.

In a potential embodiment, the air scenting device according to the present disclosure may exhibit the alternative or additional feature that the housing comprises a plurality of accommodations, and each of the accommodations is configured to accommodate at least one scent module.

In an embodiment having a control and the plurality of accommodations, optionally, at least one of the plurality of accommodations comprises an identification detector, such as an RFID reader, to determine for the control an identity of a perfume in a module having an RFID and accommodated at any particular time in the accommodation having the identification detector.

In such an embodiment having at least the plurality of scent module accommodations, optionally, the housing comprises a single air and scent perfume mixing chamber with more than one of the plurality of accommodations, and a valve between at least one of the plurality of accommodations and the single air and scent perfume mixing chamber.

After the above more generic description of the subject of the present disclosure, a detailed description is provided below of a limited number of preferred embodiments referring to the appended drawing. Only a limited number of embodiments is described, since the potential of the present disclosure with respect to alternatives is practically boundless. However, although the below described embodiments are at the time of the present disclosure preferred, these are by no means intended to allow any unwarranted limitation on the scope of protection to any of the features from the following embodiment description to result in a more restricted scope of protection for embodiments of the present disclosure than that according to the appended independent claims. In the appended drawing, throughout separate figures, the same or similar reference signs may be employed to indicate the same or similar elements, features, components or aspects. In the appended drawing:

FIGS. 1, 2 and 3 respectively show a perspective view, a behind view and a below view of first embodiment of an air scenting device according to the present disclosure;

Figure 6:
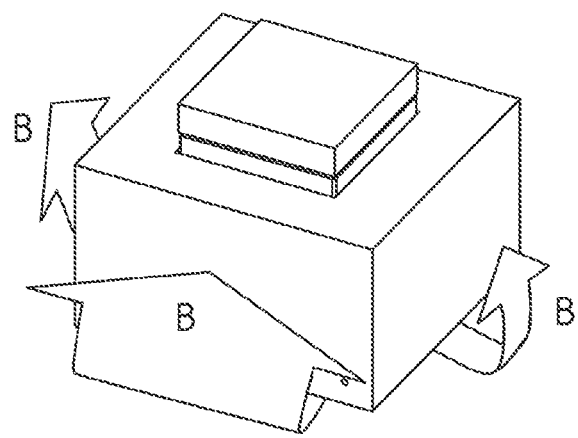
Figure 7:
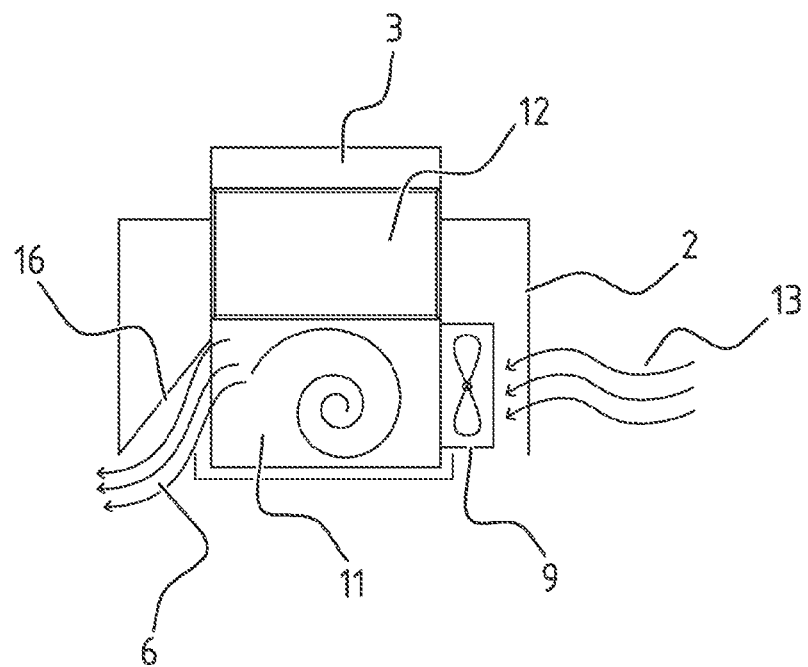
Figure 8:
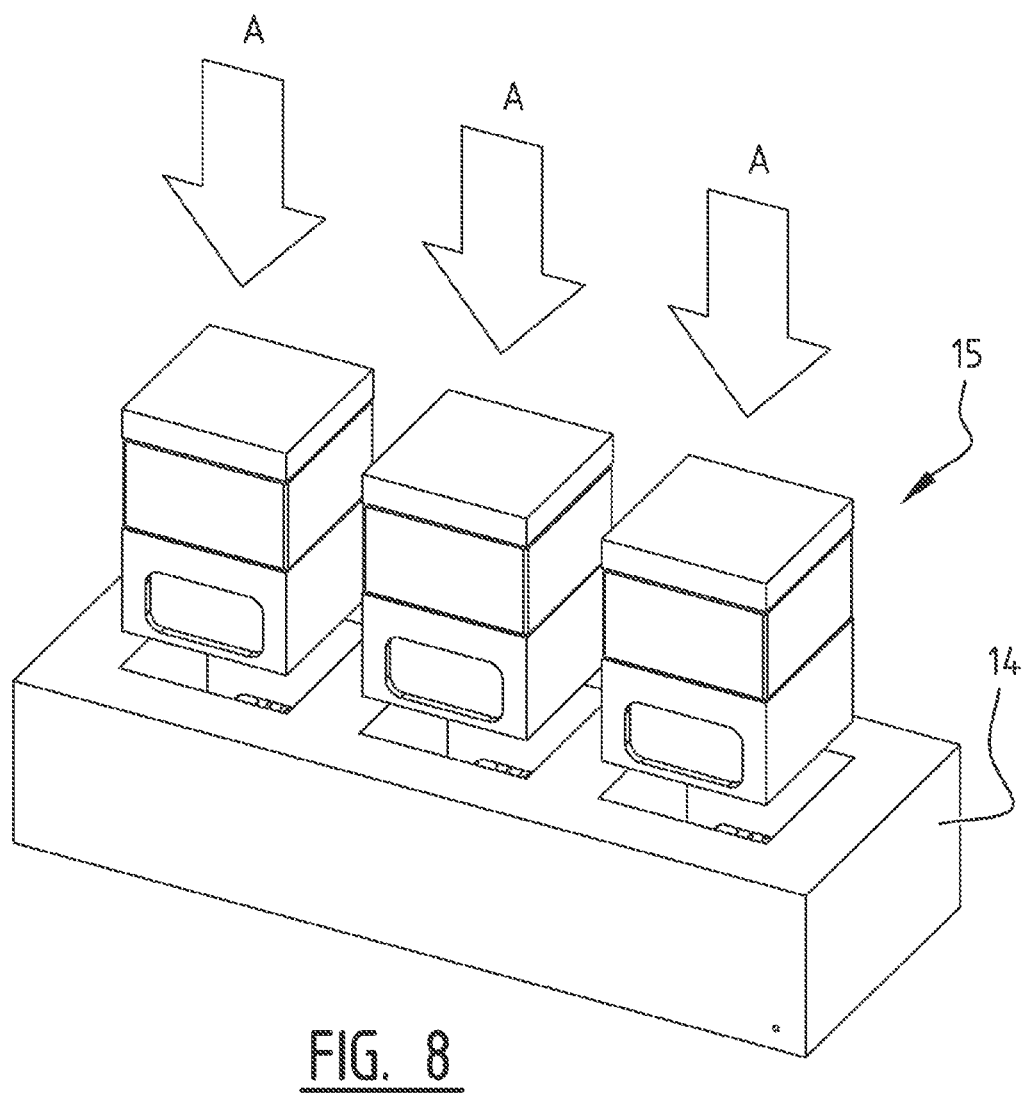
Figure 9:
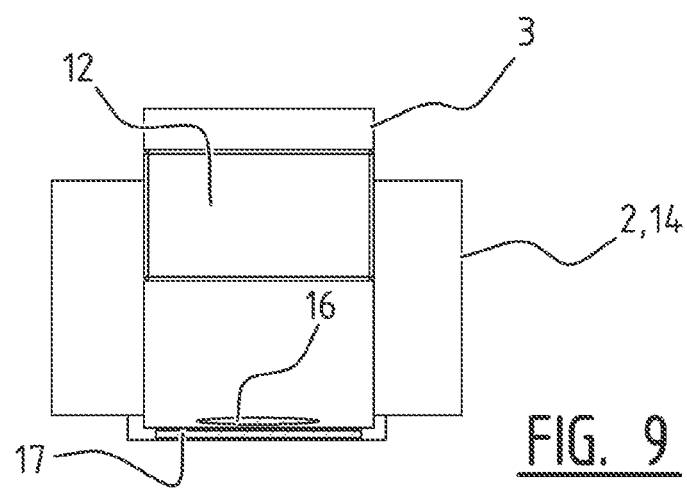
Figure 10:
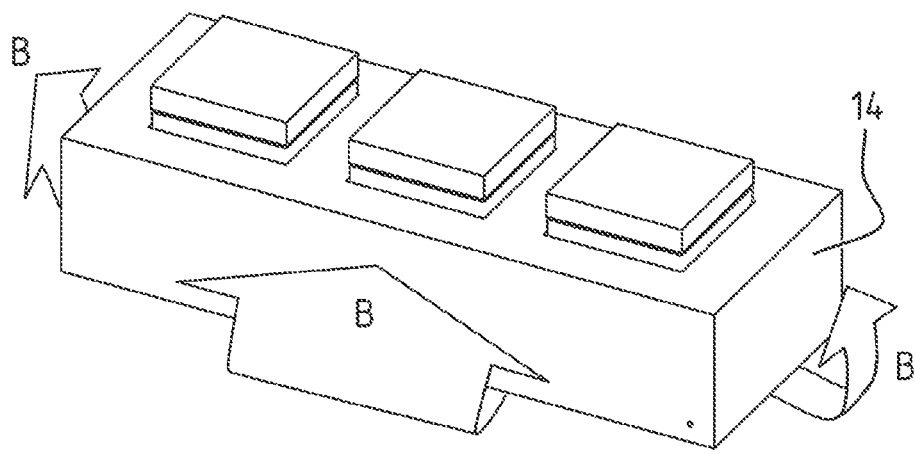
Figure 11:
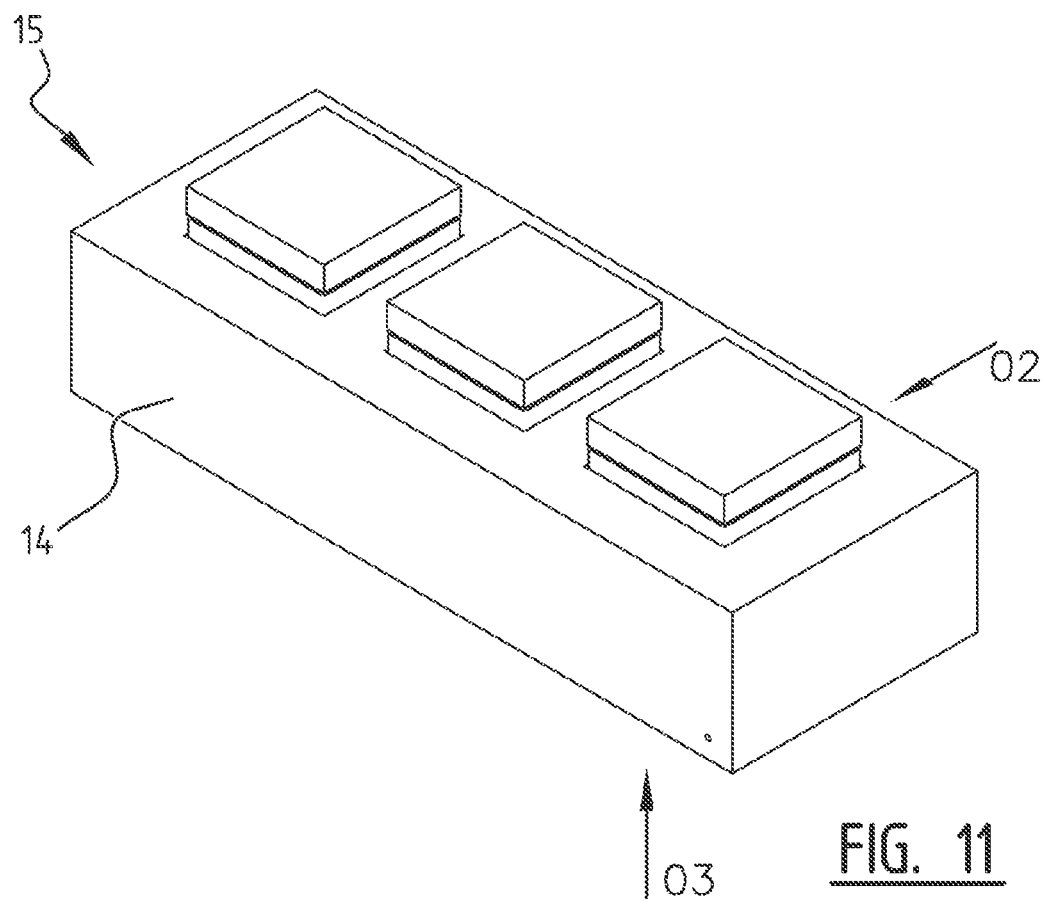
Figure 12:
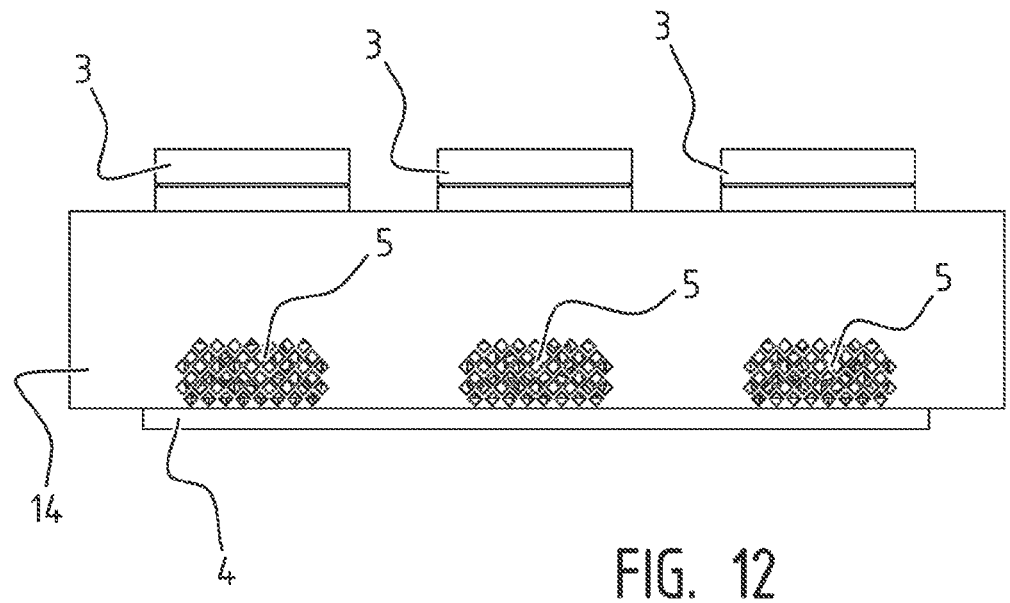
Figure 13:
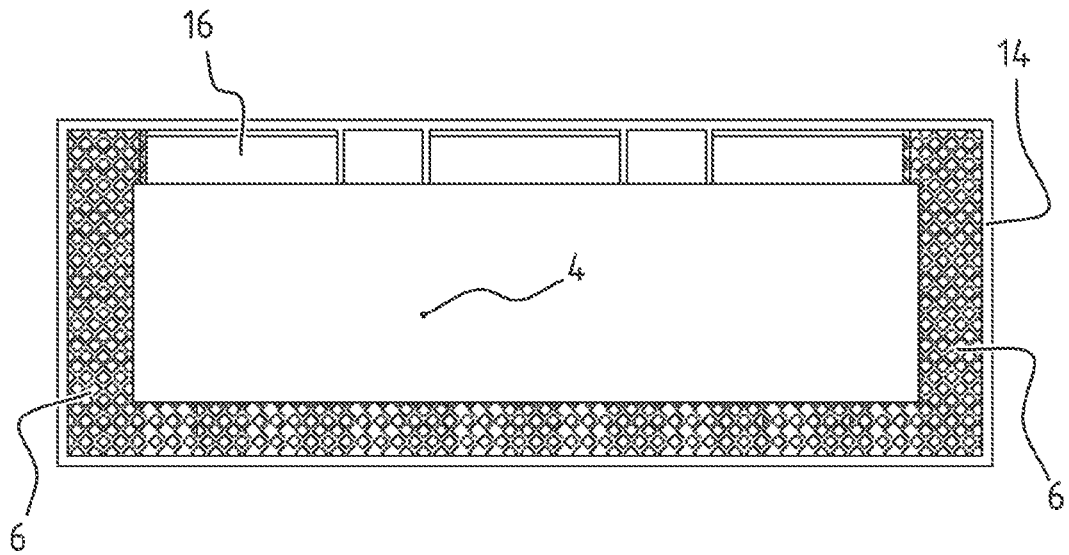
Figure 14:
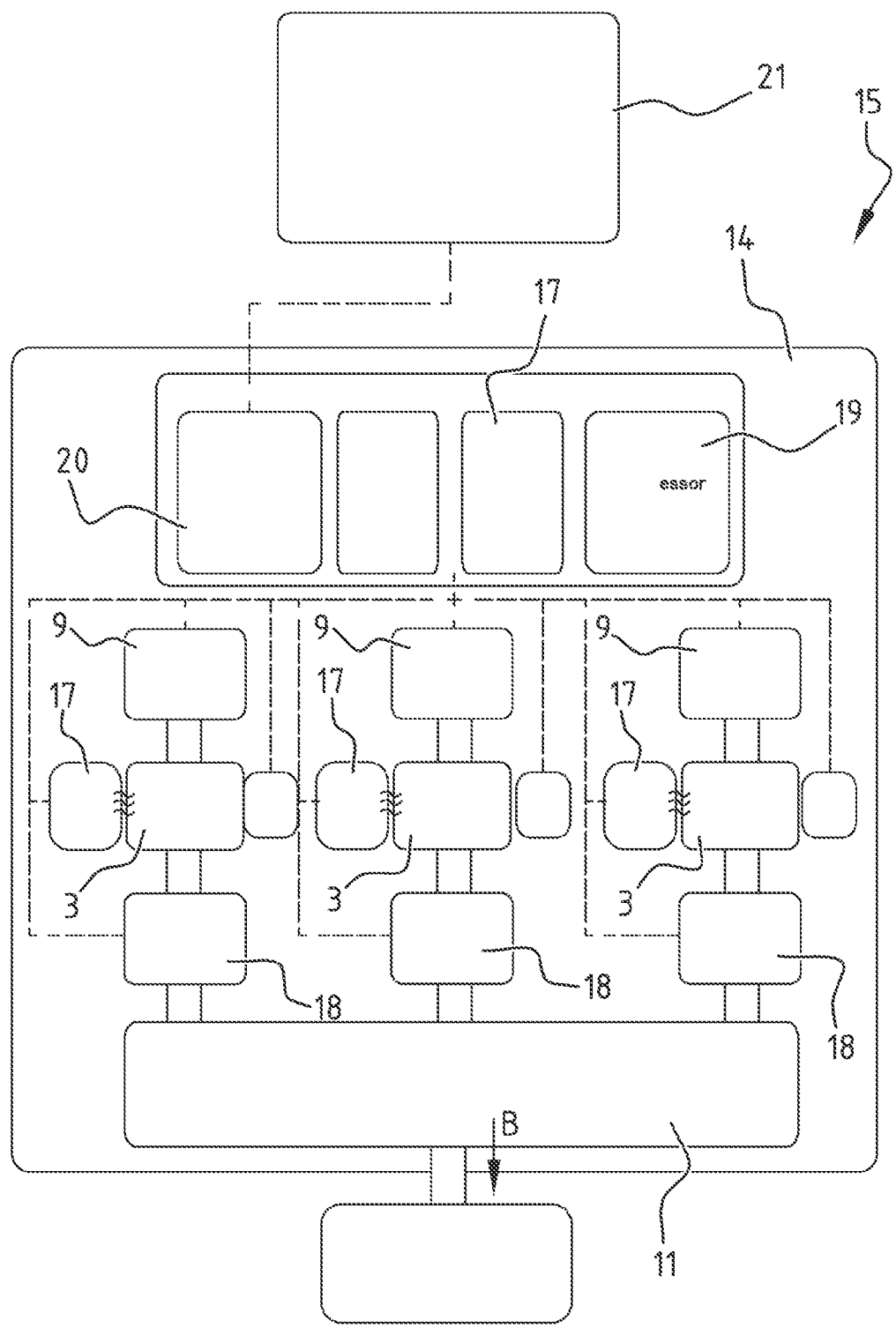
Figure 15:
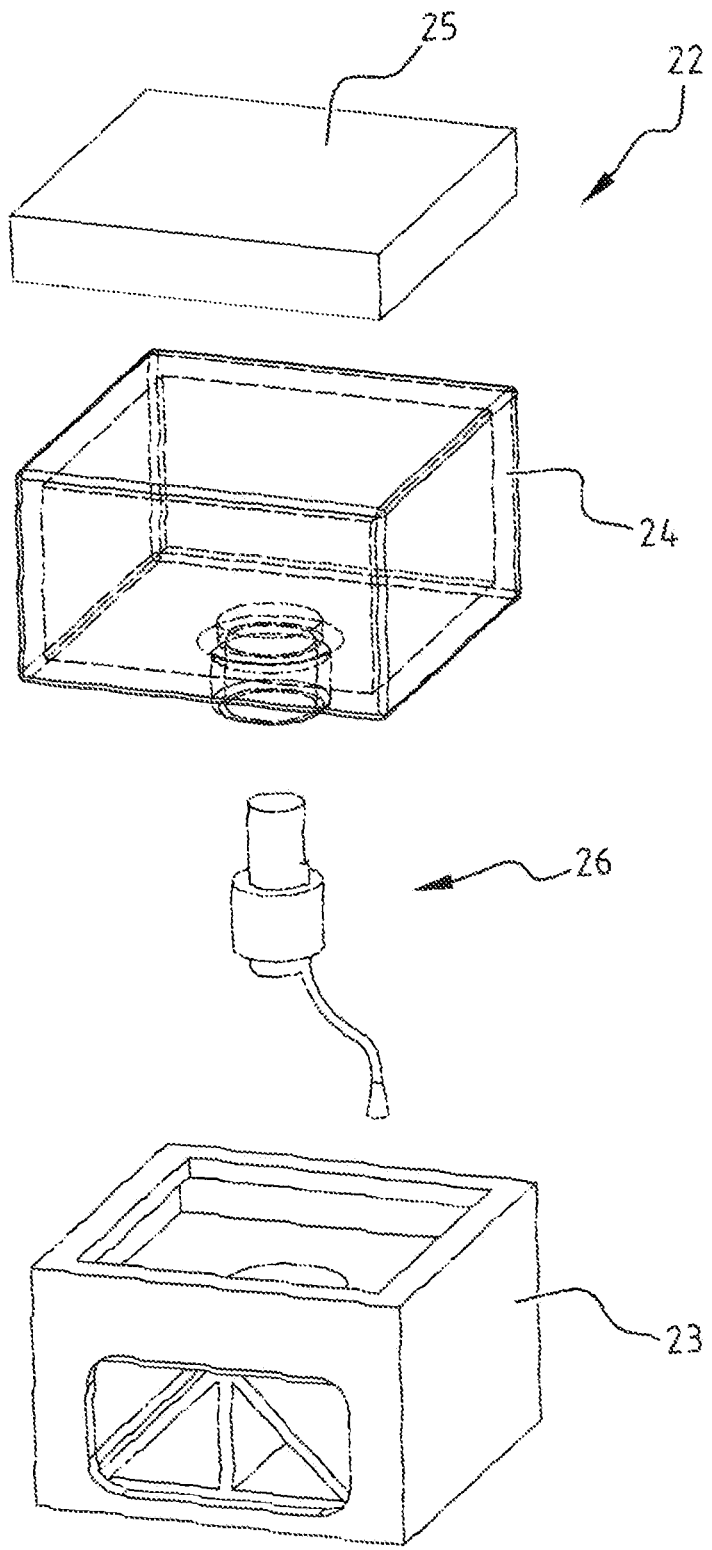
Figure 16:
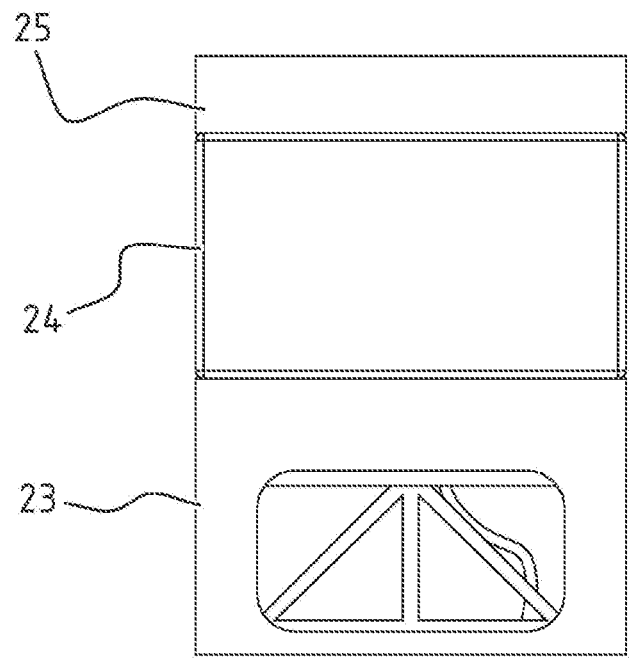
Figure 17:
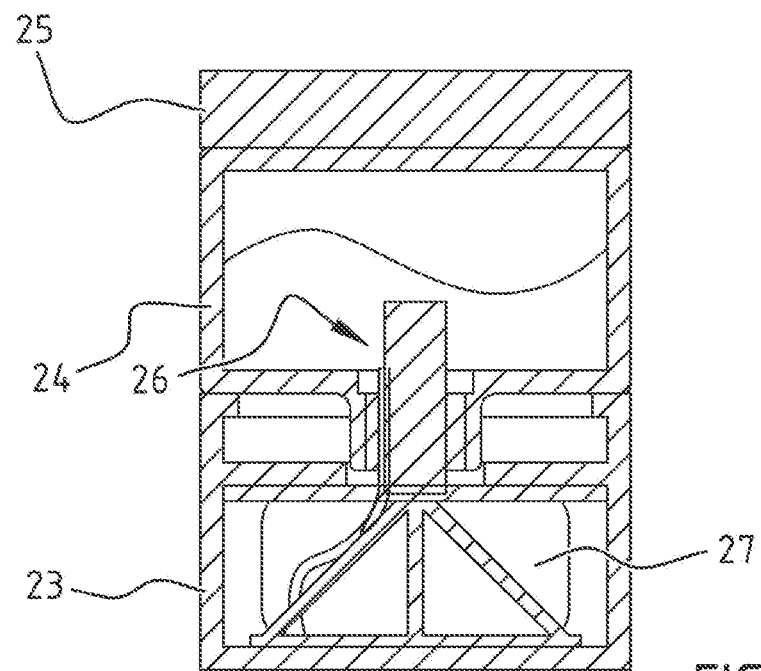
Figure 18:
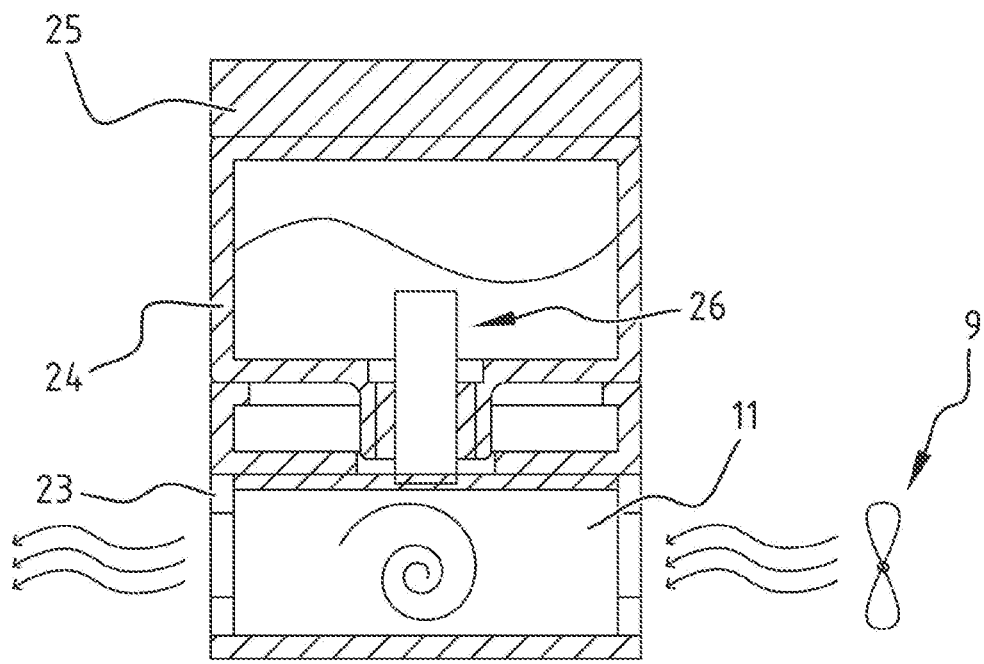
Figure 19:
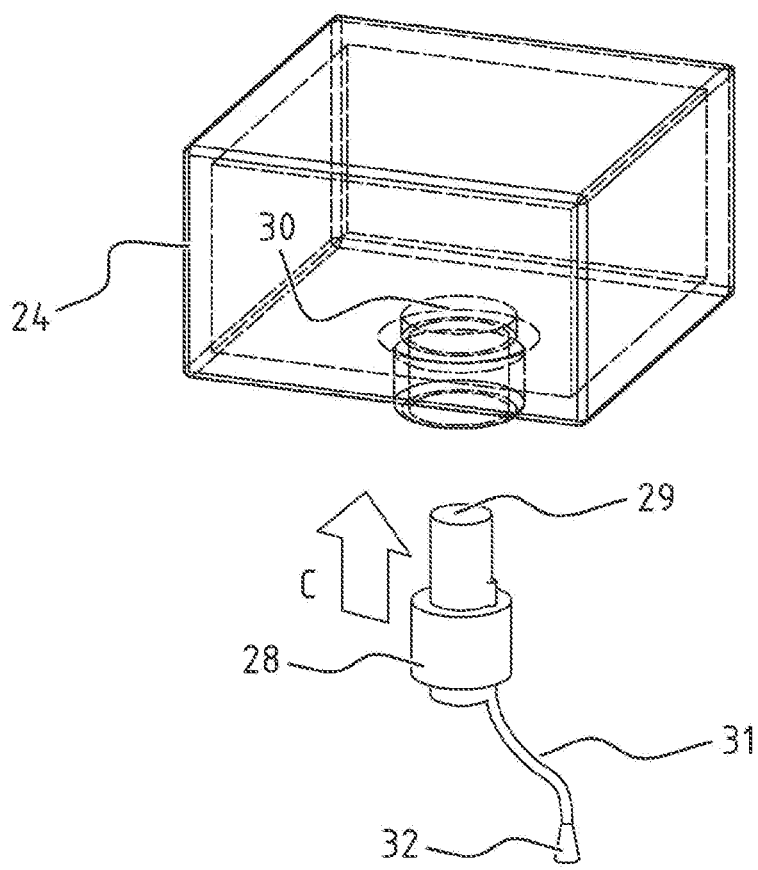
Figure 20:
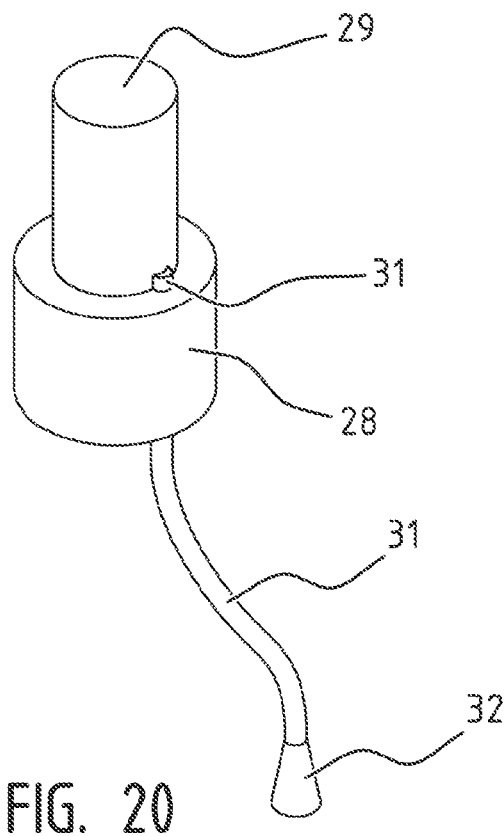
Figure 21:
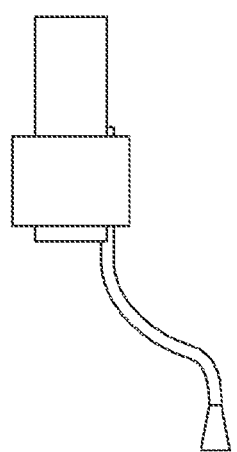
Figure 22:
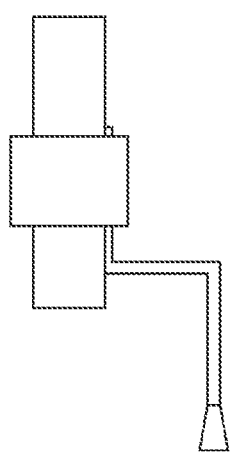
Figure 23:
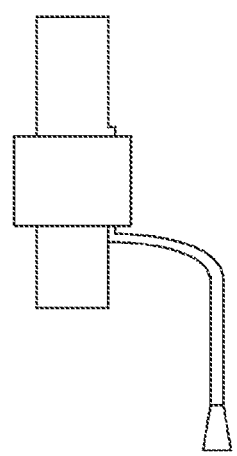
Figure 24:
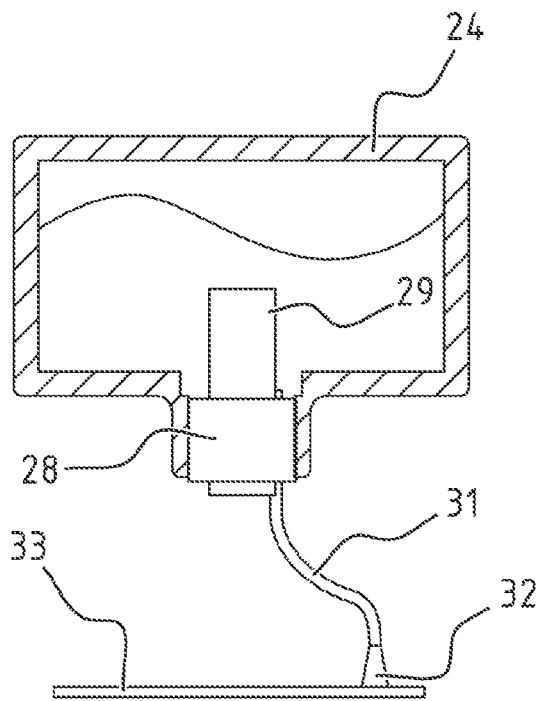

FIGS. 6 and 7 respectively show a perspective view and a cross sectional view of the air scenting device in the first embodiment and in operation;

FIG. 8 shows a perspective view of an air scenting device having a plurality of accommodations for a plurality of scent modules;

FIG. 9 shows the optional use of ID's in the form of for example RFID markers, to determine the nature of a scent perfume in a module in an accommodation;

FIG. 10 shows the air scenting device of FIG. 8 and having a plurality of accommodations for a plurality of scent modules, in operation;

FIGS. 11, 12 and 13 respectively show a perspective view, a behind view and a below view of the embodiment of FIG. 8 of an air scenting device according to the present disclosure;

FIG. 14 shows a schematic view of an exemplary embodiment of an air scenting device according to the present disclosure;

FIG. 15 shows an exploded view of an embodiment of an air scenting device according to the present disclosure;

FIGS. 16, 17 and 18 show respectively a front view, a front cross section and a side cross section of the device of FIG. 15 in an assembled state;

FIG. 19 schematically shows a step in assembling the air scenting device of FIG. 15;

FIGS. 20 and 21 respectively show a perspective view and a side view of a component of the embodiment of FIG. 15 enlarged and in more detail;

FIGS. 22 and 23 show side views of alternative embodiments of or for the component of FIGS. 20 and 21;

FIGS. 24-27 respectively show different stages of functioning of a scent perfume extracting mechanism;

FIGS. 28-32 alternative embodiments relative to a portion of the present disclosure with respect to FIG. 17; and FIGS. 33-38 show a further embodiment of an air scenting device according to the present disclosure.

Figure 1:
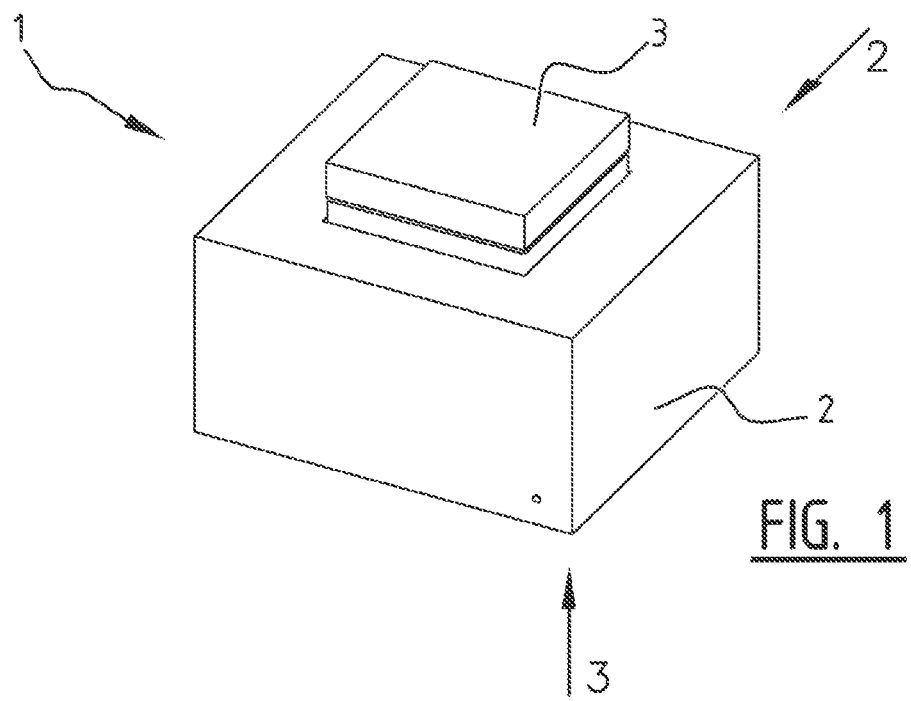
Figure 2:
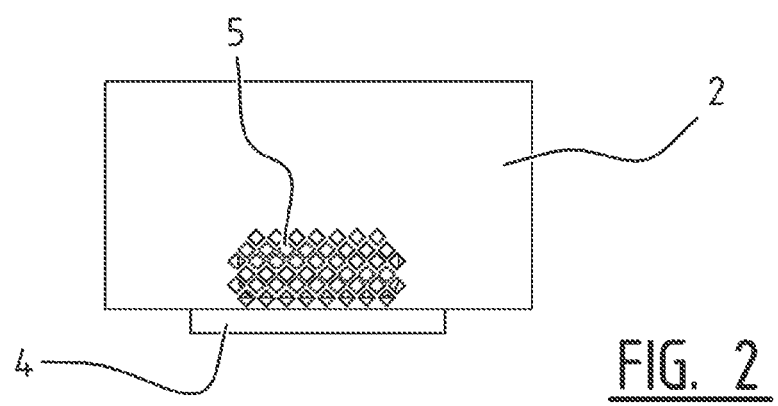
Figure 3:
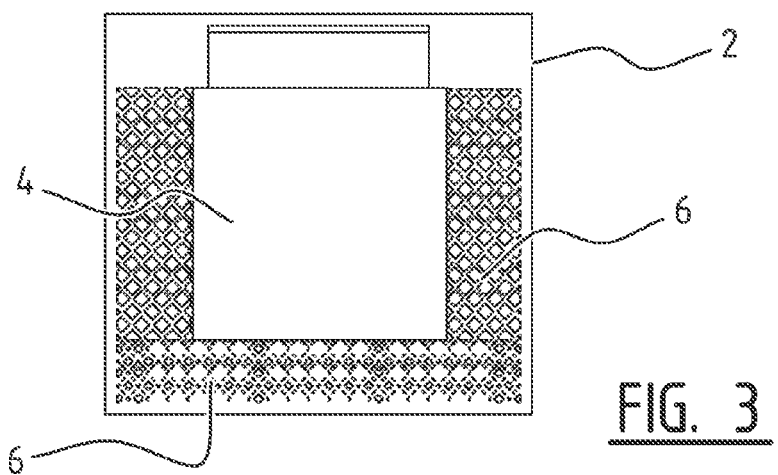

FIG. 1 shows a first embodiment of an air scenting device 1 according to the present disclosure, which comprises a housing 2, which defines an accommodation for a scent module 3 lowered into the accommodation, as will be described in more detail herein below. The back view of FIG. 2 shows that housing 2 is arranged on a foot 4, and that in the back of housing 2 a grid or opening 5 is provided, through which air to be scented can be drawn into housing 2. The bottom view of FIG. 3 also shows housing 2 and foot 4, with additionally blowout grids 6. The foot 4 may configured to support housing 2 thereon. The foot 4 has a smaller horizontal circumferential size than the housing and the outflow opening is arranged at least partially around the foot. The outflow opening may have a blowout grid 6, or define an unrestricted opening. The outflow opening may be arranged in the foot, as well, if interiors of the housing 2 and foot 4 are in open air flow connection. In case the outflow opening is under the housing 2, at least partially around the foot 4, or in a side wall of foot 4, the blowout opening may be at least partially and preferably fully hidden from sight.

Figure 4:
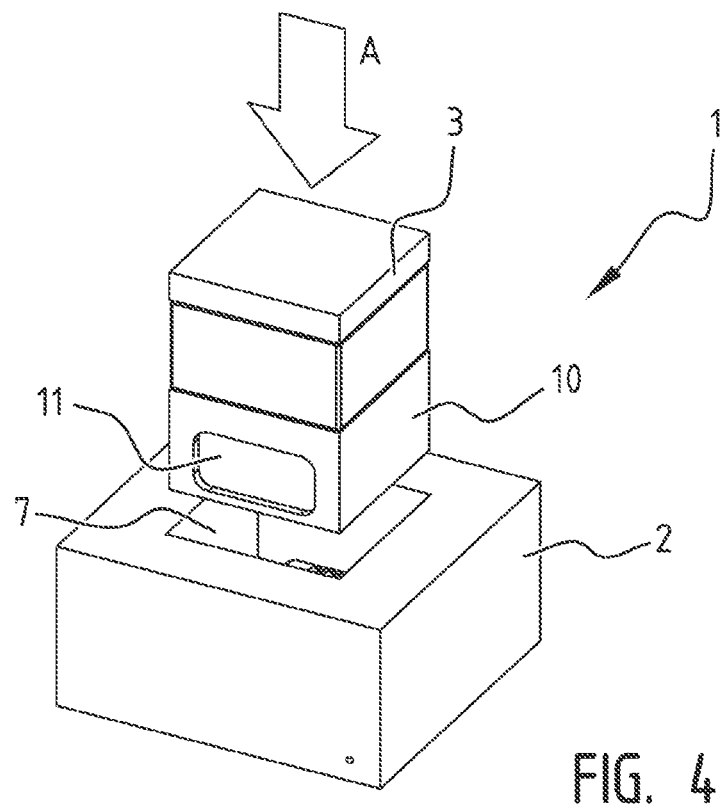
FIG. 4 shows introduction of a scent module into an accommodation of a housing of the air scenting device in the first embodiment.
Figure 5:
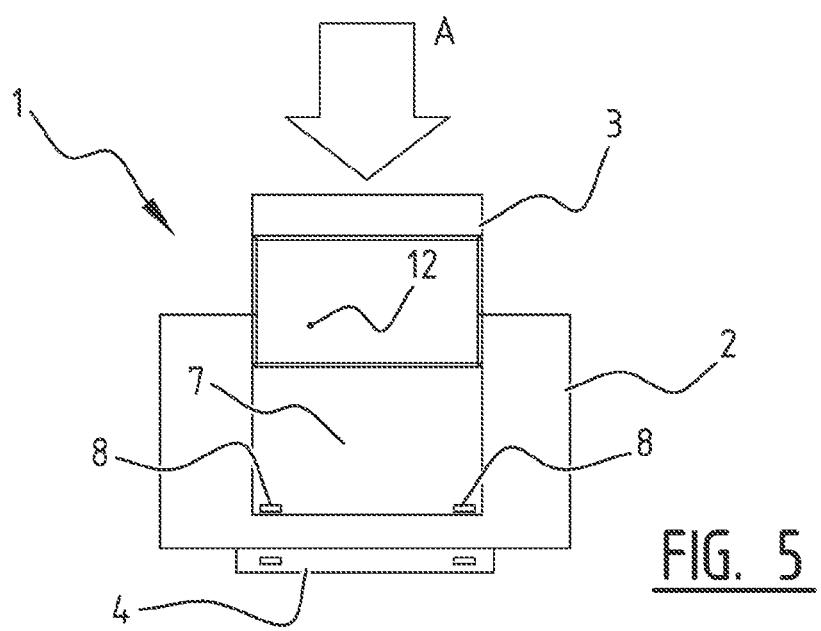
FIG. 5 shows an example of a latch, coupling or engaging of the scent module in the accommodation.

The perspective view of FIG. 4 and the cross sectional view of FIG. 5 more clearly show the accommodation 7 within housing 2, into which scent module 3 is to be lowered in the direction of arrow A. At the bottom of accommodation 7, a pair of magnets 8 is provided to latch, lock or engage scent module 3 and keep the scent module 3 firmly restrained within the accommodation 7. Above, it was indicated in relation to the bottom view of FIG. 3, that at the underside of housing 2, blowout grids 6 are provided. These allow scented air from a mixing chamber to be expelled in the direction of arrows B, as shown in FIG. 6. From the representation of FIG. 4 it can be seen, that scent module 3 comprises an open base 10, which is inserted into accommodation 7 first. Open base 10 defines, in combination with the confines of accommodation 7 in housing 2, a mixing chamber 11. Scent module 3 further comprises a scent perfume container 12, from which scent perfume is drawn into mixing chamber 11, in a manner, of which an example will be described herein below. It is additionally noted, that a fan 9 is provided at grid or opening 5, within the housing 2, but fan 9 could also be arranged outside of any housing, as shown in FIG. 18, which will be described herein below. In advance it is already noted here, that a fan may even be entirely omitted, within or outside of housing 2, 14, for example if the device 1, 15 is to be positioned at a location of a draft or other air flow.

When the fan 9 is in operation, turbulence is created within the mixing chamber 11 as a consequence of which scent perfume from container 12 is thoroughly mixed with an airflow 13, which is drawn into mixing chamber 11 from outside of housing 2. Mixed air and scent perfume are consequently expelled from the mixing chamber in an airflow along arrow B through blowout grids 6. In particular in the embodiment of FIG. 7, the airflow out through blowout grids 6 is enhanced by a guide plate 16, which is arranged internally of housing 2, to define a blowout duct in combination with the blowout grids 6.

In FIGS. 8, 10 essentially the same functioning is shown, relative to FIGS. 4, 6, but in relation to a different embodiment, wherein housing 14 of a scenting device 15 comprises a plurality of accommodations, allowing a plurality of scent modules to be introduced therein. FIGS. 11-13 correspond in the same manner with FIGS. 1-3. After introducing scent modules 3, generated scented air flows are expelled out of housing 14 in the direction of arrows B.

In relation to this embodiment it is noted that in particular FIG. 9 relates to an optional addition for determining the precise nature of scent perfume in any one container 12 of a scent module 3. At a predetermined position, in FIG. 9 at the bottom of the accommodation and in an assembled state of scent module 3 in housing 2, 14, three comprises an ID 16, for example and RFID tag, and housing 2, 14 comprises at a corresponding location and ID reader 17. Since in the embodiment of FIGS. 8, 10 a plurality of scent modules 3 can be introduced into corresponding accommodations 7, an air scenting device may be capable of preparing desired combinations or mixtures of scents, as will be described herein below, for which it is extremely beneficial, if the device 1, 15 is capable of determining the precise nature of the contents of any container 12. Consequently, desired combinations or mixtures can be expelled in the direction of arrows B. However, it should be noted here that even in a singular embodiment, such as the embodiment of FIGS. 1-7, it may be beneficial that the device 1, 15 is informed of the precise nature of the contents of the container 12 of scent module 3, to be able to regulate an outflow of scent perfume in correspondence with the strength or noticeability of the scent perfume that is actually in any embodiment of a device 1, 15 according to the present disclosure.

In the embodiment of FIG. 14, optional heat elements 17 are added. Further, optional valves 18 are added. Heat elements 17 and valves 18 may be under control of a processor 19, into which an appropriate program can be loaded. Such a program can be designed to take into account strength or noticeability of scent perfume is in individual modules 3—detectable using an ID for each scent at or in every module 3, and/or resulting combinations or mixtures. Additionally and/or alternatively, such a program can be designed to take into account input from a user, for which any other number of input/output features may be provided in the device 15, for example, a modem 20. In particular, a possibility can be created for a user to input commands for the device 15, for example over the Internet, in particular using for instance an app, executed on a mobile device, such as a smart phone, a tablet computer, laptop computer or the like, for which an online portal or smart home system 21 can provide access.

The control of device 15 may act on the airflow generator or fan 9 to speed up or slow down. Likewise, the control of device 15 can drive the heat elements 17 to individually heat up or cool down, and/or the control of device 15 can control each of the separate valves 18 to open or close more or less. These and other control options can be utilized to influence the scented airflow, that is mixed in the chamber 11 and output to the user in the direction of arrow B.

An important feature of the embodiment of FIG. 14 is that a single mixing chamber 11 is provided within housing 14 of device 15. It is in particular noted that scent perfume from each of the separate scent modules 3 is transferred from the modules 3 to the mixing chamber 11. Therein, the mixing of scents with air is accomplished. An optional mixer (not shown) could additionally be provided in the mixing chamber.

It is self evident that scent modules 3 are not intended to have an open base 10, like in the embodiment of FIGS. 1-7, at least in order to define mixing chamber 11, since the mixing chamber 11 in the embodiment of FIG. 14 is common for a plurality of scent modules 3. Having the common mixing chamber allows for additional control over generated scented air, in particular when a plurality of different scented perfumes from a plurality of different scent modules 3 are to be mixed with air to arrive at the generated output flow of generated scented air.

FIG. 15 shows an exploded view of a scent module 22, having a carrier structure 23, a scent perfume extracting mechanism 26, a scent container 24 containing at least initially a scent perfume, and a lid or top 25. The lid or top 25 may be mostly cosmetic, i.e. provided for appearance purposes, but may also serve as a functional closure of an open top of scent container 24. FIG. 16 shows a front view, FIG. 17 shows a cross section in front view (the same direction as that of FIG. 16), and FIG. 18 shows a cross section view in a direction perpendicular to the viewing direction of FIGS. 16, 17. FIGS. 17 and 18 show ribs 27 of the carrier structure 23. These ribs 27 can serve to strengthen the carrier structure 23 and/or to guide scent perfume from the scent container down to the mixing chamber 11. Additionally or alternatively, ribs 27 may be formed from scent carrying material, which may be structural only, or may be configured to be impregnated or drenched with scent perfume, to release the scent perfume to an air flow through the mixing chamber 11, when fan 9 or any other airflow generator is controlled to be in operation. Alternative configurations of the ribs 27 in similar front cross sections as FIG. 17 are shown in FIGS. 28-32.

As indicated above, scent perfume is released from the scent container 24, using scent perfume extracting mechanism 26, of which an example and alternate embodiments for specific parts and/or components thereof is shown in FIGS. 19-27.

The shown exemplary scent perfume extracting mechanism 26 comprises an air controlled dripping mechanism 28, to which a scent absorber 29 is connected in order to be inserted into the scent container 24, through a valve construction 30, which is designed to remain closed, unless scent absorber 29 is inserted there through in the direction of arrow C in FIG. 19. Scent perfume from the interior of container 24 may be absorbed by scent absorber 29 and passed down into dripping mechanism 28. The dripping mechanism normally continues to drip scent perfume (FIGS.

Figure 25:
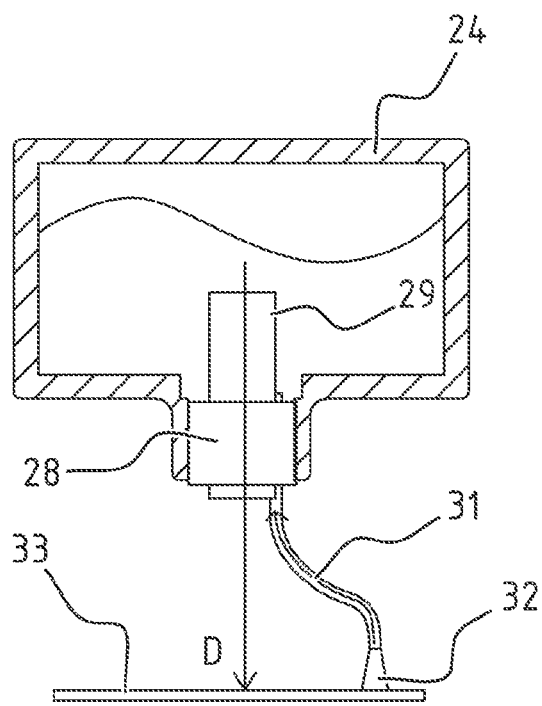
Figure 26:
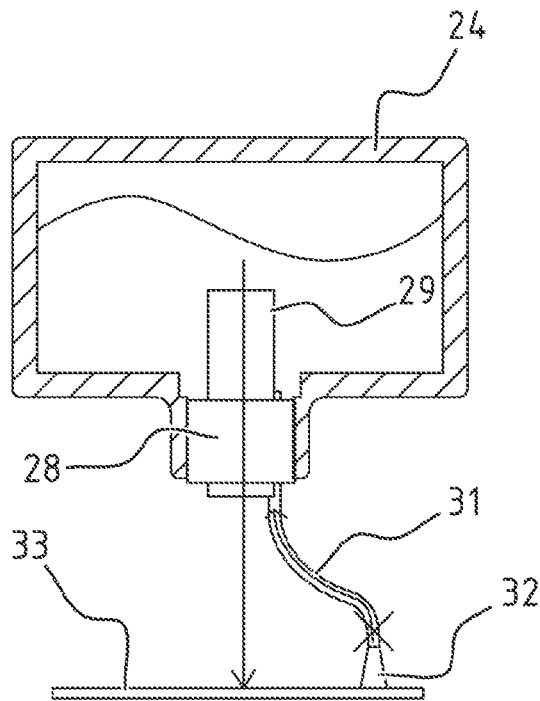
Figure 27:
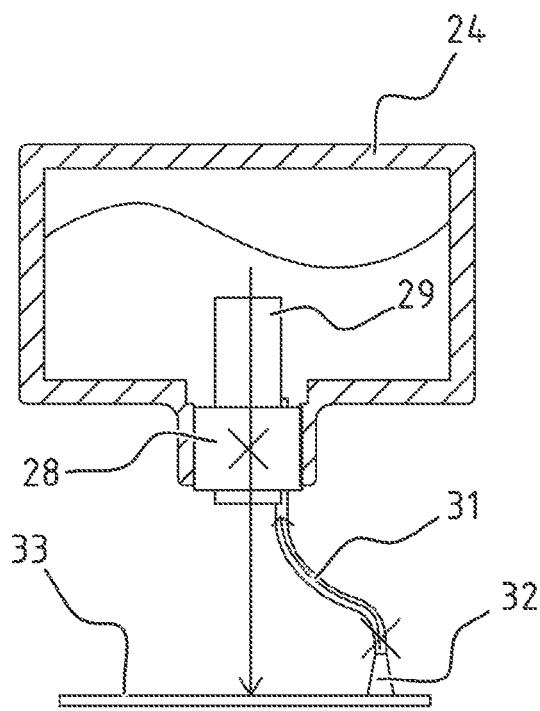
Figure 28:
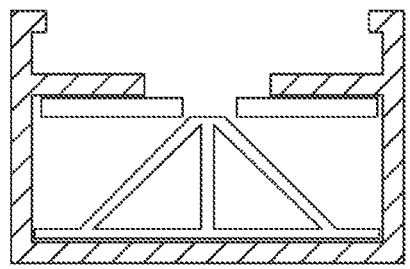
Figure 29:
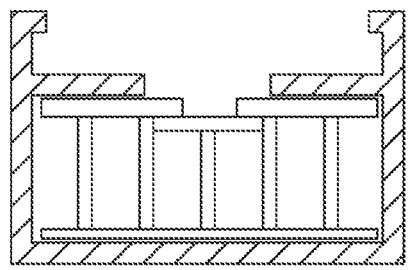
Figure 30:
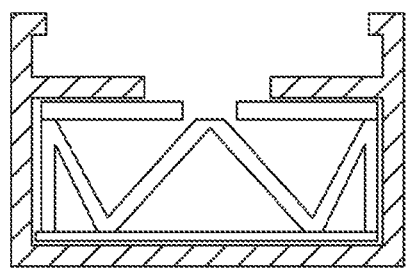
Figure 31:
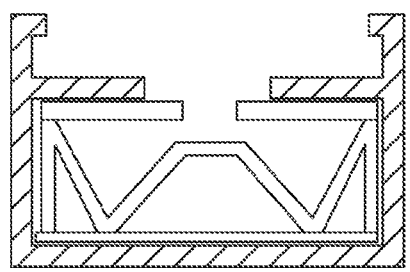
Figure 32:
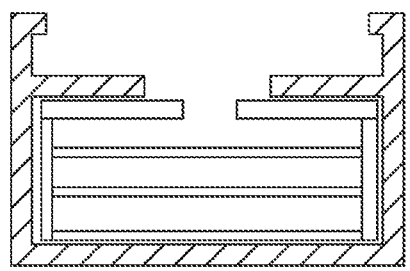
Figure 33:
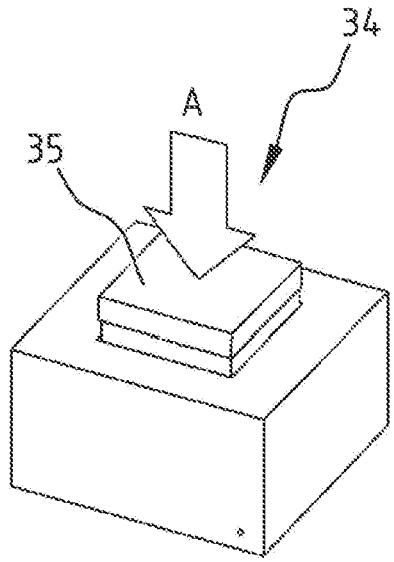
Figure 34:
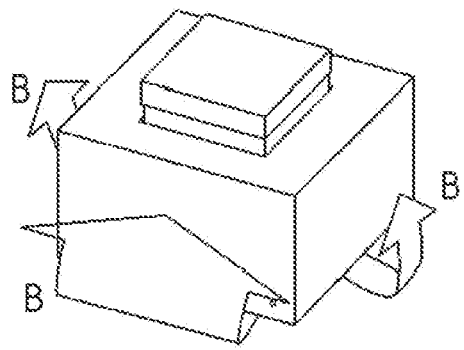
Figure 35:
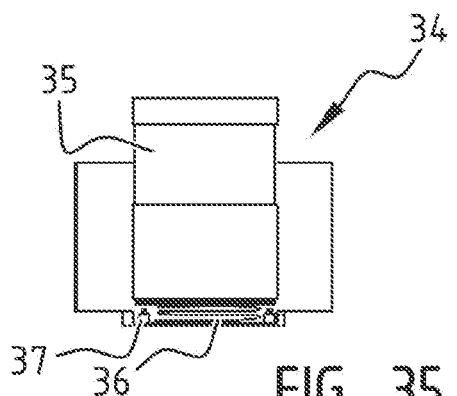

24, 25) onto scent carrying material 32 in the direction of arrow D in FIG. 25. Further, the scent perfume extracting mechanism 26 comprises an air duct 31 with a nozzle 32. Nozzle 32 is arranged on the scent carrying material 33, which may for instance be fibrous, to absorb or be drenched with the scent perfume deposited thereon by dripping mechanism 28. When the scent carrying material 33 is drenched to saturation (FIG. 26), no more air can pass through scent carrying material and up into nozzle 32 and air duct 31. In this manner, the nozzle 32 arranged on scent carrying material 33 acts as a check valve in that passage of air up into the container is prevented when the scent carrying material 33 is saturated, and enabled as long as the scent carrying material 33 is dry enough to allow passage of air up into the container through air duct 31. Alternately, a check valve comprising for instance a float valve or the like can be specifically provided to enhance the thus described check valve function. The air duct 31 passes air through or along dripping mechanism 28 up into the interior of container 24, as long as the scent carrying material 33 is sufficiently dry, so that when no air is let up into the container through nozzle 32 and air duct 31, when scent carrying material 33 has become saturated, and then the extraction of scent perfume will halt (FIG. 27) as a consequence of under-pressure, that is thereby generated inside the container 24.

FIGS. 21, 22 and 23 show exemplary alternative embodiments for the sub-assembly of scent absorber 29, dripping mechanism 28, air duct 31 and nozzle 32, relative to for example FIG. 20, which shows an enlarged representation of said sub-assembly, compared with the representation in FIG. 19.

The embodiment of FIGS. 33-38 adds a particular functionality of an override or boost, enabling the user to force the air scenting device 34 to expel scented air. In particular, the container 35 can be pressed down in the direction of arrow A, which denoted the same direction as the orientation, in which a container 35 is introduced into the air scenting device 34 in for instance FIG. 4. When the container 35 is pressed down in the direction of arrow A, the air scenting device 34 is made to expel extra scented air in the direction of arrows B in FIG. 34.

Figure 36:
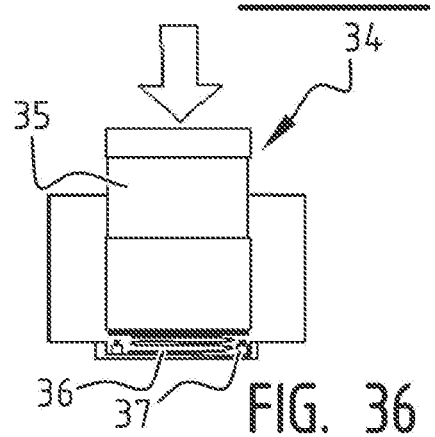
Figure 37:
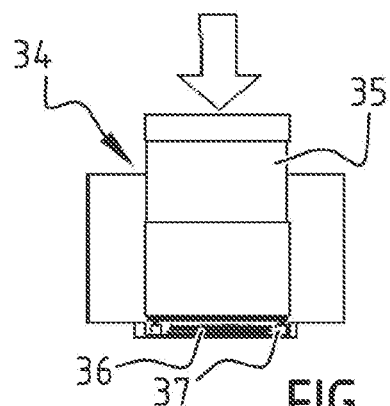
Figure 38:
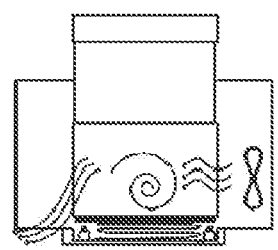

This may be achieved in any number of ways. Merely as an exemplary embodiment, FIGS. 35-38 show that the air scenting device 34 accommodates container 35 resting on a spring 36. When the container 35 is pressed down against the spring force of the spring 36, as shown in FIG. 36, the bottom of the container will come into contact with switches 37, as shown in FIG. 37. A single switch 37 may be provided, or instead of one or more switches 37, the bottom of the container may carry an electrically conducting strip (not shown) enabling electrical conduction between two contacts (not shown). In any case, when a switch is operated, fan 38 is activated to drive scented air from the air scenting device 34. It is considered special, simple and elegant that the container 35 can be employed as an operator for the switch(es) 37 (or contacts), to enable a user to generate a boost of scented air.

It is to be noted that for some, if not all of the components, aspects and element described herein, the boundaries there between can be flexible. For example, the scent carrying element 33 is to be counted as a part of the scent extracting mechanism, but if the material thereof contributed to the structure of the mixing chamber 11, it can indeed also form part of the mixing chamber, the same as the above described function of ribs 27, which could also be part of the drenchable scent carrying material 33. The controllable features of the dripping device can also, in an alternative embodiment, be utilized to allow for scent strength control, to restrict the amount of any one scent to be freed into the space or the room of a home or a building.

In addition, the following is noted here: air scenting devices in accordance with the present disclosure can furnish an entirely new olfactory sensation in the home or the work place. The disclosure provides for a personalized selection of preferred scent selection, as well as mixing different personally preferred scents. Where the one end user would prefer to be subjected to a fresh scent, such as mint, another end user would prefer heavier scents, like cinnamon. Embodiments of the present disclosure can cater to this demand, in a much more personalized manner than a scent candle or a scented oil flask with a scent absorbing element lick a straight wick, to free scents into the room or space of a building. The disclosure allows for setting of strength of scents as well as a more free selection of scents to be used. Also, the device can easily be turned on and off, at random or according to control input from an end user, in particular if the electronic control is embodied.

Further, in particular with the devices according to the present disclosure, which have a plurality of accommodations for plural scent containers or modules, preselected grouped scents can be made available to end users. The end user may even fine tune such preselections to their precise taste. To add to the experience for end users of being able to set their environment to detail, an app or other control program on a computer, tablet, smart phone or the like, may contribute to the attractiveness of the concept of the present disclosure.

Regarding the optional integration of electronics into the concept of the present disclosure, it is noted here that the embodiment of FIG. 14 may comprise an integrated circuit board, comprising the above described elements and components. However, a wireless connection, such as Wifi, Bluetooth, Zigbee or GSM, may be omitted in favour of a wired connection. Both wired and wireless connections allow an end user to have control over the function of the air scenting device or the assembly thereof with a scent module.

Embodiments according to the present disclosure may comprise a high-tech air displacement system, wherein a pump, fan or other air displacement element may be entirely controlled using for example a PWM (pulse width modulation) based algorithm, depending on circumstances and requirements of specific manufacturers and/or end users.

The device may comprise a detection for detecting fill of the containers of scent, in order to inform the end user, via the aforementioned app or other control software, that any particular container is reaching depletion, to allow the end user to secure and install a replacement module or container.

The device may comprise a venturi construction instead of or in addition to a fan or pump. Likewise, the device may contain or comprise an atomiser or at least a fine spray nozzle, to dispense scent into the mixing chamber. Such depletion warnings could also be directed at a manufacturer, for instance if an end user has a contract whereby the manufacturer is bound to supply new scent modules, when installed containers or modules near depletion, thus ensuring that the scent sensation of the present disclosure is not disrupted for the end user.

Above, the personalized offer of scents and in particular mixes thereof has been referred to. However, in addition it is noted here that the referenced app could be replaced by a "regular" computer program to run on a PC or on a laptop computer. However, the inventors of the present disclosure feel that embodiments of the present disclosure allow perfect integration into a smart home system, to then as a new feature include scent sensation.

The scent module is, in the appended drawing, square in shape, but could be round or have any arbitrary other shape or form, like cylindrical or the like.

Above, reference was already made to an end user's taste and preference with respect to the nature of scents to emanate from the device. It is further noted here, that scent groups may be selected by an end user or offered by a manufacturer, based on beforehand known end user preferences, such as heavier scents like cinnamon, or fresher scents like mint. The system of the present disclosure further preferably has prior knowledge of an end user's preferences, and could to this end contain a non volatile memory to store at least one profile with reference to the types of kinds of scents preferred by at least one of the end users. The device can then preferably switch between end users to adapt the environment in the room quickly and without any discontinuation between end user profiles. Further, the device may contain—or the app or computer program—may have a user interface to provide recommendations to end users, based on some input of their preferences.

The invention claimed is:

1. An air scenting assembly, comprising:
   a scent container which at least initially contains a scent perfume, and
   a scent perfume extracting mechanism, which is configured to release scent perfume from the scent container, wherein said scent perfume extracting mechanism comprises:
      a scent perfume absorbing element insertable into said scent container,
      a scent carrying material,
      a dripping mechanism arranged onto said scent perfume absorbing element, said dripping mechanism is configured to deposit scent perfume from the scent container onto said scent carrying material, and
      a limiter to restrain extraction of scent perfume from the scent container, wherein the limiter comprises an air duct between the scent perfume absorbing element and the dripping mechanism, and the limiter is air flow controlled, wherein one end of said air duct is placed inside said scent container, and wherein the other end of said air duct is connected to a nozzle, said nozzle being arranged on said scent carrying material so that when said scent carrying material is drenched to saturation, no more air can pass through said scent carrying material and up into said nozzle and said air duct, and so that when the scent carrying material is dry enough passage of air through said air duct is allowed.

2. The assembly according to claim 1, wherein the scent carrying material is a fibrous material.

3. The assembly according to claim 1, wherein the air duct is configured to pass air through or along dripping mechanism up into the interior of container, as long as the scent carrying material is sufficiently dry.

4. The assembly according to claim 2, wherein the air duct is configured to pass air through or along dripping mechanism up into the interior of container, as long as the scent carrying material is sufficiently dry.

5. The assembly according to claim 1, wherein ribs are formed from scent carrying material.

6. The assembly according to claim 1, wherein the scent container is provided with a lid or top.

7. The assembly according to claim 1, wherein the assembly comprising a mixing chamber which encloses the scent carrying material.

* * * * *